Oct. 4, 1955 L. HAGLER Plant Pat. 1,424
NECTARINE TREE
Filed Jan. 11, 1955
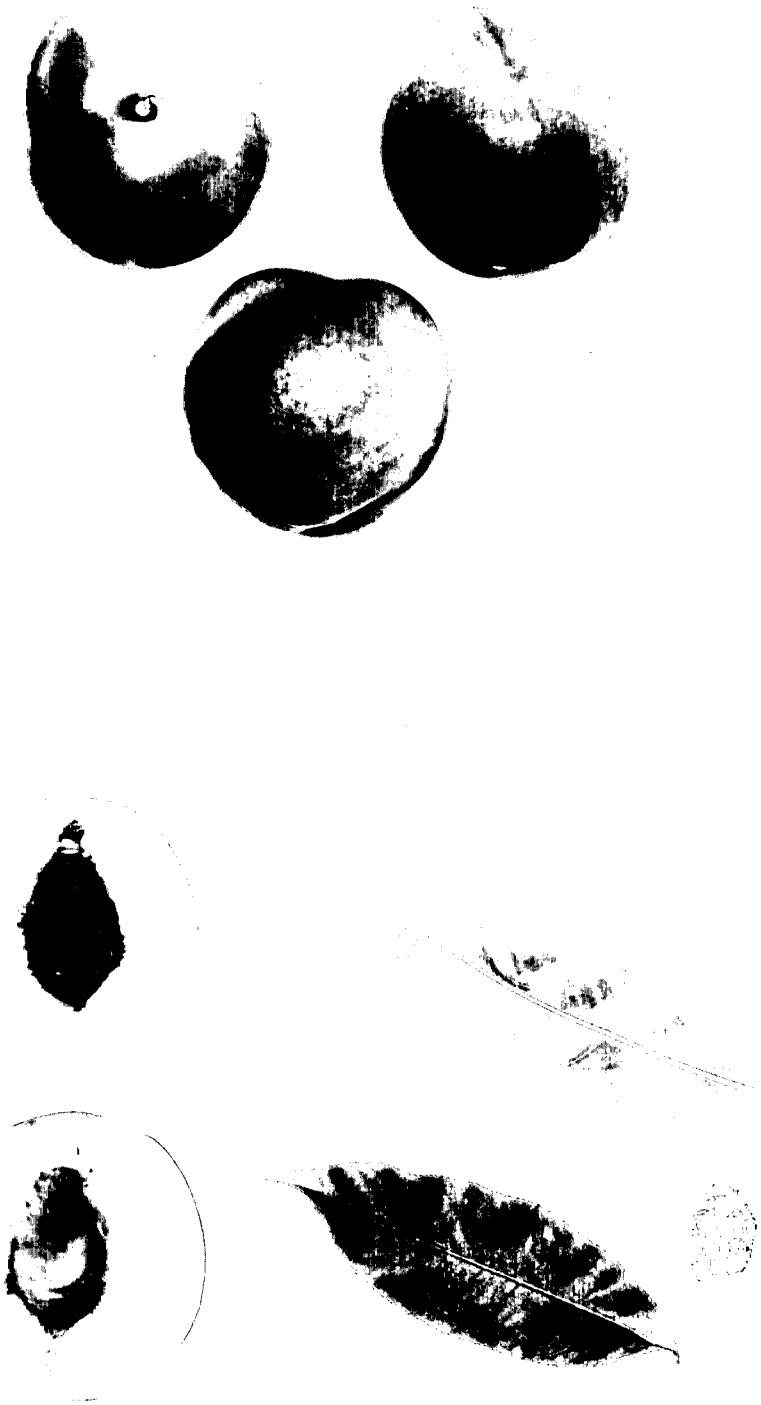
Inventor.
Lisle Hagler
By: Robb & Robb
Attorneys.

United States Patent Office

Plant Pat. 1,424
Patented Oct. 4, 1955

1,424

NECTARINE TREE

Lisle Hagler, Visalia, Calif.

Application January 11, 1955, Serial No. 481,287

1 Claim. (Cl. 47—62)

The present invention relates to a new and distinct variety of nectarine tree of the yellow-fleshed clingstone type, which was discovered by me as a sport on a "Le Grand" nectarine tree in my cultivated orchard in the western part of Tulare County, near Visalia, California.

At the time of my discovery of the sport above referred to, I was growing in my orchard some 20 acres of the nectarine variety known as "Le Grand" (Plant Patent No. 549). The sport appeared on a sucker which had been left for the purpose of shading other limbs, and my attention was directed to the sport by virtue of the fact that the fruit of the sport ripened considerably later than that of the surrounding trees. Continued observation of the sport, as well as asexual reproduction thereof, as performed by me by budding the same in my orchard near Visalia, California, confirmed that the late-ripening characteristic of the sport was fixed and transmissible by asexual reproduction. In addition to this important characteristic, my continued observations, as well as the asexual reproductions of the sport, showed that the new variety was further characterized by a unique combination of other outstanding features which definitely distinguish the new variety from its "Le Grand" parent, and from all other varieties of which I am aware, these additional features including a superior and more attractive coloring of the fruit, firm yellow flesh of very fine and smooth texture, absence of stringiness of the flesh except for a slight stringiness about the stone, relatively high sugar content, rich flavor resembling that of the variety "Early Crawford" (unpatented), good shipping qualities for both local and distant markets, and good canning qualities. All of these characteristics, taken together with the late-ripening habit of the fruit (about 4 weeks later than the fruit of "Le Grand"), make my new nectarine variety especially desirable and outstanding for commercial fruit production.

The accompanying drawing shows typical specimens of the fruit of my new variety as observed towards the opposite ends thereof and from the side, with an additional fruit specimen shown in cross-section with the stone appearing in one section and the cavity appearing in the other section, together with typical specimen leaves respectively showing the upper and lower surfaces thereof, and a small, fragmentary section of the bark of the tree, with all of the views depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Parentage: Sport of "Le Grand."

Propagation: Holds its distinguishing characteristics through succeeding propagations by budding.

Locality where grown and observed: Western part of Tulare County, near Visalia, California.

Dates first and last picking: About August 23rd to about September 5th.

Tree: From medium to large size; upright; dense; vase-formed (topped); hardy; very productive; regular bearer.

*Trunk.*—Medium stocky.

Color of bark—brown, with plum shadings.

*Branches.*—Medium stocky.

Color—Gray-green.

Lenticels—None.

*Leaves.*—Large (length about 7 inches and width about 1⅜ inches; acuminate; leathery; evenly and finely serrated; with fine veins; semi-glossy; acutely pointed; smooth.

Color—Upper side: Fern Green, Plate 0862, with slight variations of lighter shades; under side: Fern Green, Plate 0862/2, with slight variations of lighter shades.

Petiole—Length about ⅜ inch; thickness about 1/16 inch.

Glands—Kidney-shaped at base of leaves; evenly divided, with one on each side; length about 1/32 inch; width about 1/64 inch. Color—Yellow-green.

Stipules—None.

Flowers:

*Blooming period.*—Buds develop about March 8th; full bloom begins about March 15th and ends about March 22nd.

*Size.*—About 1 inch in diameter.

*Color.*—Medium pink.

Fruit:

*Size.*—Large.

Axial diameter—About 3⅛ inches.

Transverse diameter—About 3¼ inches.

*Form.*—Uniform; globose.

*Suture.*—Distinct; shallow; extends from base to apex over entire circumference.

*Ventral surface.*—Equal.

*Cavity.*—Rounded; elongated in suture plane, with suture showing on both sides.

Depth—½ inch.

Breadth—¼ inch.

Markings—None.

*Base.*—Rounded.

*Apex.*—Short; depressed.

Pistil point—None.

*Stem.*—About ½ inch long; medium caliper; pubescent; glabrous; strong adherence to stone.

*Skin.*—Medium thickness; tough; tenacious to flesh; no down; no tendency to crack. Color—From Lemon Yellow, Plate 4/1 to Lemon Yellow, Plate 4/2, with considerable coloring of Cardinal Red, Plate 822, the latter in some areas being sometimes underlaid with yellow, and in other areas with an intense shade of black.

*Flesh.*—Color—Aureolin Yellow, Plate 3/2. Surface of pit cavity—Color—Scarlet, Plate 19, with some lighter and some darker variations.

Fibres—Few.

Amygdalin—Moderate; juice abundant.

Texture—Firm; very fine and smooth; stringiness absent except for slight stringiness about stone.

Ripens—Evenly.

Flavor—Mild.

Aroma—None.

Eating quality—Very good.

Stone: Adheres to flesh over entire surface along both dorsal and ventral edges and over upper half of sides; nominal fibres.

*Size.*—Medium (length about 1¼ inches; breadth about 1 inch; thickness about ¾ inch).

*Form.*—Oblong.

*Base.*—Straight.

*Sides.*—Equal.

Surface—Irregularly furrowed.

*Ridges.*—Jagged toward base.

*Pits.*—Elongated (length about ⅞ inch; width about ½ inch; thickness about 3/16 inch).

*Dorsal edge.*—With shallow grooves.

*Color.*—Chrysanthemum Crimson, Plate 824, shaded in some areas with Black and in other areas with Brown.

*Tendency to split.*—Slight.

Use: Good for practically all uses, including market, culinary, canning and dessert.

Keeping quality: Good.

Shipping quality: Very good.

I claim:

A new and distinct variety of nectarine tree of the yellow-fleshed clingstone fruit type, substantially as herein shown and described, characterized particularly as to novelty by the good coloring of its fruit, firm yellow flesh, the very fine and smooth texture of the flesh and the absence of stringiness thereof except for a slight stringiness about the stone, the relatively high sugar content of its fruit and the rich flavor thereof resembling the flavor of the fruit of "Early Crawford" (unpatented), the good shipping qualities of its fruit and consequent suitability thereof for both local and distant markets, the good canning qualities of the fruit, and the late-ripening habit of the fruit—about 4 weeks later than the parent variety "Le Grand."

No references cited.